United States Patent [19]

Hattori et al.

[11] 4,344,317
[45] Aug. 17, 1982

[54] AIR-FUEL RATIO DETECTING SYSTEM

[75] Inventors: Tadashi Hattori, Okazaki; Yoshiki Ueno, Aichi, both of Japan

[73] Assignee: Nippon Soken, Inc., Nishio, Japan

[21] Appl. No.: 174,446

[22] Filed: Aug. 1, 1980

[30] Foreign Application Priority Data

Sep. 14, 1979 [JP] Japan .................................. 54-118154

[51] Int. Cl.³ ............................................ G01N 27/12
[52] U.S. Cl. ........................................ 73/23; 123/440
[58] Field of Search .................... 73/23; 123/440, 489; 60/276, 285

[56] References Cited

U.S. PATENT DOCUMENTS

| 4,140,085 | 2/1979 | Rabus et al. | 123/440 |
| 4,153,023 | 5/1979 | Asano et al. | 123/440 |
| 4,156,413 | 5/1979 | Taplin | 123/440 |
| 4,171,690 | 10/1979 | Hosaka et al. | 123/440 |
| 4,258,563 | 3/1981 | Yasuda et al. | 73/23 |
| 4,266,519 | 5/1981 | Norimatsu et al. | 73/23 |

Primary Examiner—Stephen A. Kreitman

Attorney, Agent, or Firm—Cushman, Darby & Cushman

[57] ABSTRACT

An air-fuel ratio detecting system is designed to compensate for the effects of temperature changes on the output resistance of an air-fuel ratio sensor adapted to detect the air-fuel ratio of mixture supplied to an engine from the composition of its exhaust gases so as to vary its electric resistance in accordance with the air-fuel ratio. The system further includes a current control circuit for controlling the current supplied to the air-fuel ratio sensor, an average voltage detecting circuit for detecting a rich air-fuel ratio peak voltage and a lean air-fuel ratio peak voltage and obtaining the intermediate voltage therebetween, a bias control circuit responsive to the value of the intermediate voltage so as to adjust the current control amount of the current control circuit, and a comparator responsive to the junction point voltage and the value of the intermediate voltage so as to generate an air-fuel ratio detection signal. Alternatively, the average value of the rich side peak voltage and the ground voltage or the average value of the lean side peak voltage and the supply voltage may be used as the desired intermediate voltage.

7 Claims, 5 Drawing Figures

AIR-FUEL RATIO DETECTING SYSTEM

BACKGROUND OF THE INVENTION

The present invention relates to air-fuel ratio detecting systems, and more particularly the invention relates to a system for detecting the air-fuel ratio of an engine from the composition of its exhaust gases.

Air-fuel ratio detecting systems have heretofore been proposed which, as shown for example in U.S. Application Ser. No. 018,776 entitled "Air-Fuel Ratio Detecting System" filed in the names of Hattori, et al on Mar. 8, 1979, comprises an air-fuel ratio sensor comprising mainly of a metal oxide semiconductor such as titania ($TiO_2$) which senses the air-fuel ratio A/F from the exhaust gas component, such as, the concentration of oxygen in the exhaust gases of an engine and whose electric resistance value varies in dependence on the oxygen concentration, fixed dividing resistors connected to the air-fuel ratio sensor, and a comparator circuit for comparing the voltage at the junction of the sensor and the resistors with a predetermined reference voltage so as to determine whether the air-fuel ratio A/F is greater or smaller than the stoichiometric air-fuel ratio.

However, this type of known system is disadvantageous in that since the dividing resistors are set to fixed values, in dependence on the operating temperature and aging the electric resistance value Re characteristic of the air-fuel ratio sensor changes (or shifts) on the whole as, for example, from the curve X to the curve Y in FIG. 1, thus deteriorating the detection accuracy of air-fuel ratio A/F and increasing the tendency to cause erroneous detection.

SUMMARY OF THE INVENTION

With a view to overcoming the foregoing deficiencies in the prior art, it is an object of the present invention to provide an improved air-fuel ratio detecting system capable of accurately detecting the air-fuel ratio of an engine irrespective of the operating temperature and aging of its air-fuel ratio sensor.

It is another object of the present invention to provide such air-fuel ratio detecting system in which an air-fuel ratio sensor is connected, for example, to a transistor current control circuit in place of the fixed dividing resistors connected in series with the sensor, whereby the voltage at the junction point of the air-fuel ratio sensor and the current control circuit is detected in either one or both of the rich and lean ranges of air-fuel ratios to obtain the intermediate value between the detected peak value and the supply voltage or the ground voltage or the intermediate value between the detected rich and lean peak values and thereby to control the equivalent resistance value of the current control circuit connected to the air-fuel ratio sensor in accordance with the intermediate value, and in accordance with the voltage at the junction point of the air-fuel ratio sensor and the current control circuit and the intermediate voltage a comparator circuit detects whether the air-fuel ratio is greater or smaller than the stoichiometric air-fuel ratio, thus preventing deterioration in the accuracy of air-fuel ratio detection and occurrence of erroneous detection.

It is still another object of the invention to provide such air-fuel ratio detecting system so designed that during the initial period, such as, the period immediately after the engine start where the exhaust gas temperature and the air-fuel ratio sensor temperature are relatively low and the electric resistance value Re of the air-fuel ratio sensor is high, the current control circuit is controlled in accordance with a predetermined set voltage which is also used as the comparison voltage of the comparator circuit, thus initiating the air-fuel ratio detecting operation satisfactorily.

DESCRIPTION OF THE PREFERRED EMBODIMENT

The present invention will now be described in greater detail with reference to the illustrated embodiment.

Figure 2:
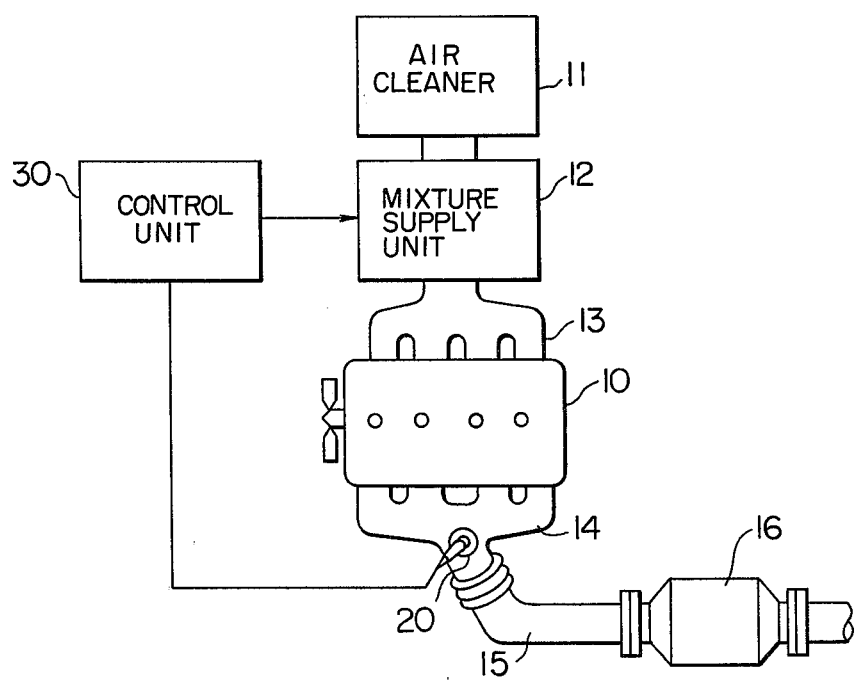
FIG. 2 is a schematic block diagram of a system incorporating the present invention.

Referring to FIG. 2 showing a system incorporating the present invention, an engine 10 is a known type of spark ignition engine which uses gasoline, LPG or the like as its fuel and it includes an intake system consisting of an air cleaner 11, an air-fuel mixture supply unit 12 and an intake manifold 13 and an exhaust system consisting of an exhaust manifold 14, an exhaust pipe 15, an exhaust gas purifying three-way catalytic converter 16 and a silencing muffler which is not shown.

The mixture supply unit 12 comprises a carburetor or a fuel injection system including a known type of air-fuel ratio adjusting means and it changes the air-fuel ratio of the produced air-fuel mixture (in the intake system) in accordance with the input electric signal. The three-way catalytic converter 16 is capable of simultaneously removing NOx, HC and CO components of exhaust gases with a high purification efficiency when a mixture of near the stoichiometric air-fuel ratio is supplied to the engine and it includes a known type of pellet or honeycomb catalyst.

The air-fuel ratio detecting system comprises an air-fuel ratio sensor 20 disposed in the joining portion of the exhaust manifold 14 and a control unit 30 for applying an electric signal to the air-fuel ratio sensor 20 and the mixture supply unit 12, respectively.

Figure 3:
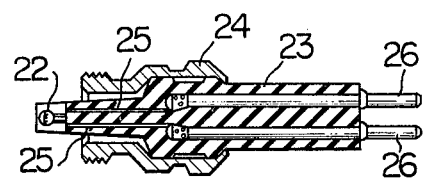
FIG. 3 is a sectional view of the air-fuel ratio sensor shown in FIG. 2.

The air-fuel ratio sensor 20 is constructed as shown in FIG. 3. In the Figure, a disk type sensing element 22 has an electric resistance value which varies in a step fashion in response to the composition, particularly the concentration of oxygen in the exhaust gases and it consists of a semiconductor of such metal oxide as titania ($TiO_2$) whose surface is covered with a catalyst such as platinum (Pt) or rhodium (Rh). The sensing element 22 is supported on the forward end of a heat resisting and electrically insulating support 23 made of a sintered alumina or the like. A heat resisting metal housing 24 is attached to the support 23, and the sensor 20 is mounted to the exhaust manifold 14 by the threaded portion of the housing 24.

Inserted into the sensing element 22 are a pair of platinum electrodes 25 which are disposed inside the support 23 and each of the electrodes 25 is electrically connected to a terminal rod 26 by way of a conductive glass. The electric resistance value of the sensing element 22 is taken out through the terminal rods 26.

Figure 1:
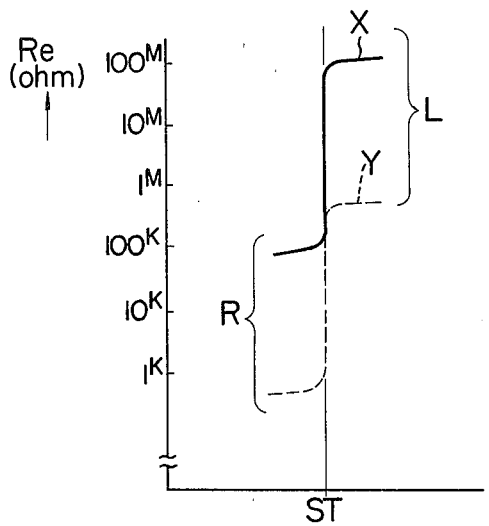
FIG. 1 is a graph showing an electric resistance value characteristic of an air-fuel ratio sensor.

As shown in FIG. 1, the electric resistance value Re of the air-fuel ratio sensor 20 varies with the air-fuel ratio A/F of the mixture so that when the air-fuel ratio A/F is greater than the stoichiometric air-fuel ratio ST (or on the lean side), the resistance value Re changes to a lean resistance value L, whereas when the A/F is smaller than the stoichiometric air-fuel ratio ST (or on the rich side), the resistance value Re changes to a rich resistance value R. Also, this electric resistance value characteristic varies (or shifts) on the whole in dependence on the operating temperature and aging of the sensor, so that in the case of a new sensor operated at a low temperature its characteristic becomes as shown by the curve X in FIG. 1, and the curve Y in FIG. 1 corresponds to that of a new sensor operated at a high temperature or that of one subjected to aging.

Figure 4:
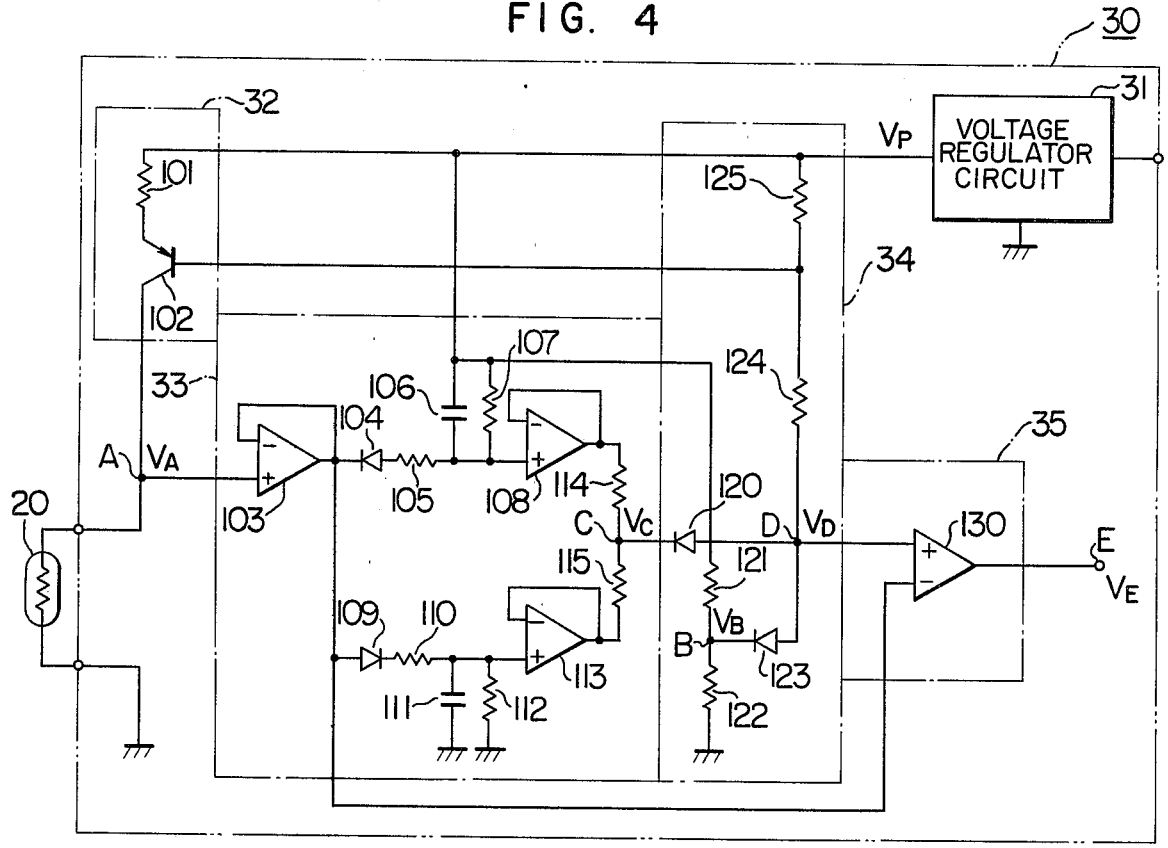
FIG. 4 is a circuit diagram showing an embodiment of the present invention.

Next, the control unit 30 will be described with reference to FIG. 4. A voltage regulator circuit 31 supplies a constant DC voltage $V_P$. A current control circuit 32 comprises a current limiting resistor 101 and a transistor 102. The collector terminal of the transistor 102 is connected to the air-fuel ratio sensor 20 whose other end is grounded. The junction point A of the air-fuel ratio sensor 20 and the transistor 102 is connected to an intermediate level detecting circuit 33.

The intermediate level detecting circuit or average voltage generating means 33 comprises a capacitor 106 adapted to be charged through a buffer amplifier 103 which is connected in a voltage follower arrangement, a diode 104 and a resistor 105, a rich peak detecting circuit including a discharge resistor 107 and another buffer amplifier 108, a lean peak detecting circuit including a diode 109, resistors 110 and 112, a capacitor 111 and a buffer circuit 113, and resistors 114 and 115 connecting the outputs of the peak detecting circuits. The intermediate value between the peak values is delivered from the junction point C of the resistors 114 and 115. A bias control circuit 34 is designed so that the previously mentioned intermediate voltage and the voltage at a point B derived by dividing the constant voltage $V_P$ through resistors 121 and 122 or a preset voltage are respectively coupled through diodes 120 and 123 to a point D through which lower one of the voltages is delivered. The circuit is also connected to the power supply through resistors 124 and 125 and the junction point of the resistors 124 and 125 is connected to the base of the transistor 102 in the current control circuit 32. A comparator circuit 35 comprises a comparator 130, whereby the output of the buffer amplifier 103 which is equal to the voltage at the junction point of the air-fuel ratio sensor 20 and the transistor 102, is compared with the voltage at the point D and the resulting A/F detection signal is generated at a point E.

Figure 5:
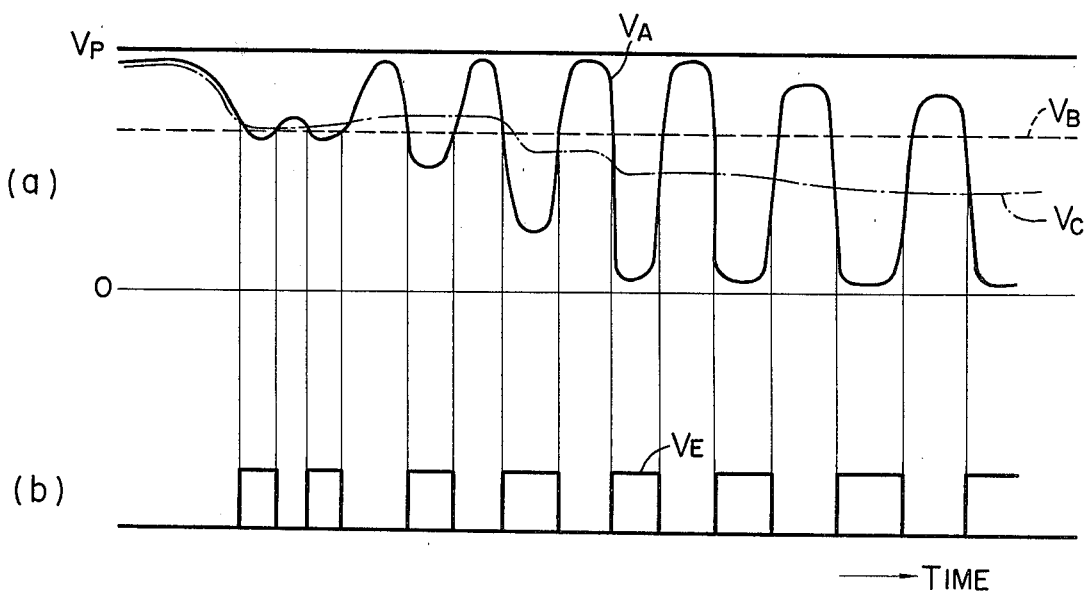
FIG. 5 shows the signal waveforms generated at various points in FIG. 4.

With the construction described above, the operation of the air-fuel ratio detecting system wil now be described with reference to FIG. 5. When the exhaust gas temperature is gradually increased, the voltage at the junction point A of the air-fuel ratio sensor 20 and the transistor 102 and the voltages at the points B, C and E vary as shown in (a) and (b) of FIG. 5. When the exhaust gas temperature is very low (as during the period just after the engine start), the electric resistance value of the air-fuel ratio sensor 20 is so high that the voltage $V_A$ at the point A is substantially equal to the supply voltage $V_P$. As the exhaust gas temperature rises gradually so that the temperature of the air-fuel ratio 20 also rises, even if the oxygen concentration of the atmosphere remains unchanged, the electric resistance value of the air-fuel ratio sensor 20 decreases gradually so that the voltage $V_A$ at the point A starts to decrease. At this time, the voltage $V_C$ at the point C has a value which is substantially equal to the voltage $V_A$ at the point A and hence higher than the voltage $V_B$ at the point B which is predetermined by the resistors 121 and 122. As a result, the voltage $V_B$ at the point B appears at the point D as the bias control voltage for the transistor 102 and as the comparison voltage of the comparator 130.

In other words, until the voltage $V_C$ at the point C becomes lower than the voltage $V_B$ at the point B, the base voltage of the transistor 102 is maintained constant thus practically holding it in the off state and the comparison voltage of the comparator 130 is also held constant. When the exhaust gas temperature rises further so that the voltage $V_A$ at the point A becomes lower than the voltage $V_B$ at the point B or the comparison voltage, the output of the comparator 130 changes from a "0" level to a "1" level and an A/F detection signal $V_E$ is generated at the point E. As a result, the mixture supply unit 12 initiates the air-fuel ratio control. After the air-fuel ratio control has been initiated, if the exhaust gas temperature is still relatively low and if the mixture is rich, the resistance value of the air-fuel ratio sensor 20 is about the same with the resistance across the emitter and collector of the transistor 102 so that the rich peak value (the minimum peak value) is not allowed to decrease to the ground level and thus the point-A voltage $V_A$ varies in the vicinity of the supply voltage $V_P$. As a result, the intermediate voltage $V_C$ is also higher than the point-B voltage $V_B$ and this voltage $V_B$ is still used as the bias control voltage for the transistor 102 and as the comparison voltage of the comparator 130.

As the exhaust gas temperature rises still further so that the rich peak value of the point-A voltage $V_A$ decreases but the lean peak value is still near the supply voltage, the intermediate voltage $V_C$ between the peaks becomes lower than the point-B voltage $V_B$ and consequently the voltage $V_C$ at the point C is used as the bias control voltage for the transistor 103 and as the comparison voltage of the comparator 130. The base voltage of the transistor 102 is decreased as compared with that obtained when the bias of the transistor 102 was controlled by the point-B voltage $V_B$, so that the emitter current of the transistor 102 is increased and the collector-emitter resistance is decreased, thus increasing the current flowing to the air-fuel ratio sensor 20. In this way, by decreasing the equivalent resistance of the transistor 102 connected to the air-fuel ratio sensor 20 in response to a decrease in the resistance value of the sensor 20 with an increase in the exhaust gas temperature, it is possible to cause the point-A voltage $V_A$ to always vary considerably in dependence on the rich and lean air-fuel ratios.

Of the circuits described so far, the intermediate level detecting circuit 33 may be caused to obtain an intermediate voltage between a rich peak voltage and the supply voltage or between a lean peak value and the supply voltage instead of obtaining an intermediate level between rich and lean peak values.

The foregoing description has included no reference to the forward voltage of the diodes since their effects on the voltages at the points A to D are not significant.

Thus, irrespective of the overall shifting in the electric resistance value Re of the air-fuel ratio sensor 20 due to the operating temperature, etc., in accordance with a "0" level A/F detection signal generated from the comparator circuit 35 it is accurately determined that the air-fuel ratio A/F is greater than the stoichiometric air-fuel ratio ST, and in accordance with a "1" level A/F detection signal it is determined the the air-fuel ratio A/F is smaller than the stoichiometric air-fuel ratio ST.

The A/F detection signal is applied to the mixture supply unit 12 through a drive circuit which is not shown, so that when the signal is a "0" level signal, the air-fuel ratio adjusting means of the mixture supply unit 12 enriches the mixture so as to decrease the air-fuel ratio A/F and thereby to cause the same to approach the stoichiometric air-fuel ratio ST.

On the other hand, when the A/F detection signal is a "1" level signal, the air-fuel ratio adjusting means of the mixture supply unit 12 decreases the richness of the mixture so as to increase the air-fuel ratio A/F and thereby to cause the same to approach the stoichiometric air-fuel ratio ST.

In this way, the air-fuel ratio A/F is always controlled at the stoichiometric air-fuel ratio ST and thus the three-way catalytic converter 16 removes NOx, HC and CO components of the exhaust gases with a high purification efficiency.

While, in accordance with the above-described embodiment, the present invention is incorporated in the system for controlling the air-fuel ratio A/F of the mixture in the intake system of an engine, the invention may be incorporated in a so-called exhaust system A/F control system for controlling the amount of secondary air supplied to the exhaust system of an engine by means of the air-fuel ratio sensor 20.

Further, while, in the above-described embodiment, the air-fuel ratio sensor and the current controlling transistor are arranged so that the transistor is connected to the power supply and the sensor is connected to the ground, their connections may be reversed so that the air-fuel ratio sensor is connected to the power supply and the transistor is connected to the ground. In this case, where the exhaust gas temperature is very low as during the period immediately following the engine start, the voltage at their junction point becomes very low in contrast to the previously described embodiment.

It will thus be seen from the foregoing description that the present invention has a great advantage that even if the electric resistance characteristic of an air-fuel ratio sensor changes due to its operating temperature, aging, etc., the detection of air-fuel ratios can be accomplished with a high degree of accuracy, and particularly when the detection of air-fuel ratios is started under low exhaust gas temperature conditions, the current control circuit is regulated in accordance with a predetermined set value and this set value is also used as the comparison voltage of the comparator, thus satisfactory initiating the air-fuel ratio detection.

We claim:

1. An air-fuel ratio detecting system for internal combustion engines comprising:
   an air-fuel sensor for sensing the composition of exhaust gases from an engine to determine the ratio of air to fuel, said sensor having an electric resistance value varying in accordance with said air-fuel ratio;
   a current control circuit for controlling the operating current of said air-fuel ratio sensor;
   means for producing an average voltage of a varying voltage at a junction point of said air-fuel ratio sensor and said current control circuit;
   a bias control circuit responsive to the value of said average voltage to adjust a current control amount of said current control circuit; and
   a comparison circuit for producing an air-fuel ratio detection signal in accordance with the voltage at said junction point and the value of said average voltage, wherein said average voltage generating means includes means for detecting a rich peak value means for detecting a lean peak voltage, and means for generating a voltage intermediate between said peak voltages.

2. A system according to claim 1, wherein said bias control circuit includes:
   means for generating a constant voltage, and
   means for selecting one of said average voltage and said constant voltage to apply the selected voltage to said current control circuit and said comparison circuit.

3. An air-fuel ratio detecting system for internal combustion engines comprising:
   an air-fuel ratio sensor for sensing the composition of exhaust gases from an engine to determine the ratio of air to fuel, said sensor having an electric resistance value varying in accordance with said air-fuel ratio;
   a current control circuit for controlling the operating current of said air-fuel ratio sensor;
   means for producing an average voltage of a varying voltage at a junction point of said air-fuel ratio sensor and said current control circuit;
   a bias control circuit responsive to the value of said average voltage to adjust a current control amount of said current control circuit; and
   a comparison circuit for producing an air-fuel ratio detection signal in accordance with the voltage at said junction point and the value of said average voltage, wherein said average voltage generating means includes means for detecting a rich peak voltage, and means for generating a voltage intermediate between said detected peak voltage and a ground voltage.

4. An air-fuel ratio detecting system for internal combustion engines comprising:
   an air-fuel ratio sensor for sensing the composition of exhaust gases from an engine to determine the ratio of air to fuel, said sensor having an electic resistance value varying in accordance with said air-fuel ratio;
   a current control circuit for controlling the operating current of said air-fuel ratio sensor;
   means for producing an average voltage of a varying voltage at a junction point of said air-fuel ratio sensor and said current control circuit;
   a bias control circuit responsive to the value of said average voltage to adjust a current control amount of said current control circuit; and
   a comparison circuit for producing an air-fuel ratio detection signal in accordance with the voltage at said junction point and the value of said average voltage, wherein said average voltage generating means includes means for generating a lean peak voltage, and means for generating a voltage intermediate between said detected peak voltage and a power supply voltage.

5. An air-fuel ratio detecting system for internal combustion engines comprising:
- an air-fuel ratio sensor for sensing the composition of exhaust gases from an engine to determine the ratio of air to fuel, said sensor having an electric resistance value varying in accordance with said air-fuel ratio;
- a current control circuit for controlling the operating current of said air-fuel ratio sensor;
- means for producing an average voltage of a varying voltage at a junction point of said air-fuel ratio sensor and said current control circuit;
- a bias control circuit responsive to the value of said average voltage to adjust a current control amount of said current control circuit; and
- a comparison circuit for producing an air-fuel ratio detecting signal in accordance with the voltage at said junction point and the value of said average voltage, wherein when the voltage at said junction point of said air-fuel ratio sensor and said current control circuit is within a predetermined range of voltages, said bias control circuit adjusts the current control amount of said current control circuit in accordance with a predetermined set voltage, and said comparison circuit compares said junction point voltage with said set voltage to generate said air-fuel ratio detection signal.

6. An air-fuel ratio detecting system for internal combustion engines comprising:
- an air-fuel ratio sensor for sensing the composition of exhaust gases from an engine to determine the ratio of air to fuel, said sensor having an electric resistance value varying in accordance with said air-fuel ratio;
- a current control circuit for controlling the operating current of said air-fuel ratio sensor;
- means for producing an average voltage of a varying voltage at a junction point of said air-fuel ratio sensor and said current control circuit;
- a bias control circuit responsive to the value of said average voltage to adjust a current control amount of said current control circuit; and
- a comparison circuit for producing an air-fuel ratio detection signal in accordance with the voltage at said junction point and the value of said average voltage, wherein said average voltage generating means includes:
- a voltage-follower buffer amplifier connected to said junction point of said sensor and said current control circuit;
- rich peak voltage detecting means including a first charging and discharging circuit connected to an output of said voltage-follower amplifier through a first-direction diode, and a first buffer amplifier connected to said first charging and discharging circuit;
- lean peak voltage detecting means including a second charging ane discharging circuit connected to the output of said voltage-follower amplifier through a second-direction diode, and a second buffer amplifier connected to said second charging and discharging circuit; and
- means for interconnecting said first and second buffer amplifiers to generate said average voltage, and wherein said bias control means includes means for controlling said current control circuit in accordance with a predetermined reference voltage and said average voltage.

7. A system according to any one of claims 1 to 6, wherein said sensor is comprised of titania.

* * * * *